United States Patent [19]

Smith

[11] Patent Number: 4,967,005

[45] Date of Patent: Oct. 30, 1990

[54] METHOD OF PREPARING ALKOXYLATED TERTIARY AMINES

[75] Inventor: Kim R. Smith, Baton Rouge, La.

[73] Assignee: Ethyl Corporation, Richmond, Va.

[21] Appl. No.: 260,511

[22] Filed: Oct. 20, 1988

[51] Int. Cl.$^5$ ............................................. C07C 93/04
[52] U.S. Cl. ..................................... 564/475; 564/480
[58] Field of Search ................................ 564/475, 480

[56] References Cited

U.S. PATENT DOCUMENTS

| 4,647,701 | 3/1987 | Gibson | 564/480 |
| 4,665,195 | 5/1987 | Stogryn | 564/480 |
| 4,745,190 | 5/1988 | Marsella | 564/480 |

FOREIGN PATENT DOCUMENTS

180455A3 10/1985 European Pat. Off. .

*Primary Examiner*—Christine M. Nucker
*Assistant Examiner*—Frederick F. Tsung

[57] ABSTRACT

A process is described for the conversion of oxyalkylated alcohols to the corresponding alkoxylated tertiary amines, such as aminated ethoxylated amines, by reaction with a secondary amine at ambient pressure and at above ambient temperature in the presence of hydrogen and a reductive amination catalyst using, as a reductive amination catalyst, metallic iridium.

9 Claims, No Drawings

METHOD OF PREPARING ALKOXYLATED TERTIARY AMINES

BACKGROUND OF THE INVENTION

This invention relates to the preparation of alkoxylated tertiary amines from oxyalkylated alcohols. More particularly, this invention relates to a catalytic process for the substantially selective conversion of oxyalkylated alcohols to alkoxylated tertiary amines wherein the oxyalkylated alcohol is brought into contact with an amination catalyst of metallic iridium in the presence of hydrogen and a secondary amine at ambient pressure and at above ambient temperatures.

It is known in the art to manufacture alkoxylated tertiary amine compounds by reacting an oxyalkylated alcohol with a secondary amine in the presence of a reductive amination catalyst.

Kesling et al., European Patent Application No. 0 180 455 discloses a process for selectively preparing alkoxylated tertiary amine compounds having the general formula:

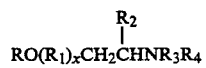

by reacting an oxyalkylated alcohol of the formula:

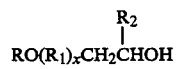

or a mixture of such alcohols, with a secondary amine of the formula $HNR_3R_4$ at a temperature in the range of from about 150° C. to 325° C. and at elevated pressures of from about 50 psig to 3000 psig in the presence of from 0.5 to 20 wt. % of an amination catalyst based on the total reaction mixture and wherein R is a straight or branched chain alkyl group having from 1 to 11 carbon atoms, a cyclic alkyl group having from 5 to 10 carbon atoms, an aryl group having up to 12 carbon atoms, or an aralkyl or alkaryl group having up to 18 carbon atoms, $R_1$ is a single unit or a series of units of the formula:

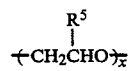

wherein each unit $R_5$ is independently selected from the group consisting of hydrogen and a straight or branched chain alkyl group having from 1 to 12 carbon atoms and x is an integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

Amination catalysts described as being useful in the process include Raney nickel, supported noble metals, and catalysts containing Cu, Cr and promoters such as nickel. Catalysts containing CuO and $Cr_2O_3$ in various ratios, Cu-Cr supported on magnesium aluminate spinel and ruthenium on activated carbon are reported to be preferred catalysts. A selectivity to the alkoxylated tertiary amine product of 98% using, as an amination catalyst, 5 wt % copper chromite supported on magnesium aluminate spinel is disclosed in Example 31.

K. R. Smith in U.S. Pat. application Ser. No. 213,346 filed June 30, 1988 discloses a catalytic process for selectively preparing alkoxylated tertiary amines by reacting an oxyalkylated alcohol with a secondary amine in the presence of a combination of Raney nickel and molybdenum.

One problem that has been associated with the conversion of oxyalkylated alcohols to alkoxylated tertiary amines in addition to obtaining high yields of alkoxylated tertiary amines at comparatively high conversion levels based on the oxyalkylated alcohol starting material, is that the oxyalkylated alcohol reactants contain ether groups which are susceptible to rupture or cleavage during a conversion operation. This not only produces unwanted cleavage products but also results in decreased yields of the desired alkoxylated tertiary amine product containing the same ether linkage present in the starting oxyalkylated alcohol reactant.

SUMMARY OF THE INVENTION

It has now been discovered that alkoxylated tertiary amine compounds of the type generally described in Kesling et al., European Patent Application No. 0 180 455 can be produced in substantially high yields at ambient pressure with minimum cleavage of the ether linkage in the oxyalkylated alcohol starting material by reacting the oxyalkylated alcohols described therein with a secondary amine in the presence of hydrogen and, as an amination catalyst, metallic iridium or metallic iridium dispersed on an inert support such as activated carbon. Employment of such a catalyst has resulted in a yield of alkoxylated tertiary amine of approximately 53% as determined by gas chromatography based on a conversion of about 81% with the production of only about 2.0% of cleavage by-products.

DESCRIPTION OF THE PREFERRED EMBODIMENT

Thus, the present invention is embodied in a method for preparing at ambient pressure an alkoxylated tertiary amine compound having the formula:

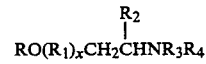

or a mixture of such amines by reacting an oxyalkylated alcohol of the formula:

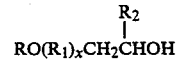

or a mixture of such alcohols, with a secondary amine of the formula $HNR_3R_4$ at elevated temperature in the presence of a catalytic quantity of an amination catalyst comprising metallic iridium, or metallic iridium dispersed on an inert support in the presence of added hydrogen wherein R is a straight or branched chain alkyl group having from 1 to 20 carbon atoms, a cyclic alkyl group having from 1 to 20 carbon atoms, a cyclic alkyl group having from 5 to 10 carbon atoms, an aryl group having up to 12 carbon atoms, or an aralkyl or alkaryl group having up to 18 carbon atoms, $R_1$ is a single unit or a series of units of the formula:

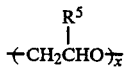

wherein in each unit $R_5$ is independently selected from the group consisting of hydrogen and a straight or branched chain alkyl group having from 1 to 12 carbon atoms and x is an integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

The process of this invention is employed in the conversion of oxyalkylated alcohols to alkoxylated tertiary amines in substantially high yields at ambient pressure with a minimum amount of cleavage of the ether linkage contained in the starting oxyalkylated alcohol material.

The alkoxylated tertiary amine compounds are prepared by reacting an alcohol or mixtures of alcohols with an alkylene oxide to prepare an oxyalkylated alcohol followed by the catalytic amination of the oxyalkylated alcohol with a secondary amine such as a dialkyl, dicyclic alkyl, dibenzyl or diallyl amine at ambient pressure in the presence of added hydrogen using, as an amination catalyst, metallic iridium.

The oxyalkylation reaction is conducted by methods well-known in the art by reacting an appropriate alcohol, such as methanol, etc. or $C_6$ through $C_{20}$ linear primary alcohols or linear primary alcohols containing various mixtures of $C_6$ through $C_{20}$ alcohols with an alkylene oxide, such as ethylene oxide, in the presence of an alkali metal or alkaline earth metal catalyst. Typical of such alcohols, which are employed in the present invention, are hexanol, the EPAL 610 ® linear primary alcohols or EPAL 810 ® linear primary alcohols which are mixtures of predominantly $C_8$ and $C_{10}$ straight chain alcohols and EPAL 1214 ® linear primary alcohols which are mixtures of predominantly $C_{12}$ and $C_{14}$ straight chain alcohols sold commercially by Ethyl Corporation.

The alcohols which may be reacted with the alkylene oxides to prepare the oxyalkylated alcohols for further processing include any aliphatic or branched monohydric alcohol containing from 1 to 20 carbon atoms, cyclic alcohols, aryl alcohols, as well as aralkyl and alkaryl alcohols as defined by R in the above formula. Specific examples include, for instance, methyl, ethyl, n-propyl, isopropyl, tert-butyl, hexyl, octyl, decyl, dodecyl, tetradecyl, benzyl alcohols, cyclohexanol, 3-methyl butanol, 1-heptanol and the like or mixtures thereof.

The alkylene oxides which may be employed to prepare the oxyalkylated alcohols include, for example, ethylene and propylene oxide and the higher alkylene oxides, i.e. containing from 3 to 12 carbon atoms as taught in Kesling et al., European Patent Application No. 0 180 455 incorporated herein by reference. A preferred alkylene oxide is ethylene oxide.

In general, the oxyalkylated alcohol formation is carried out at temperatures ranging from about 70° C. to 150° C. under moderately elevated pressures in the presence of an alkaline-reacting material or catalyst such as sodium, potassium and calcium.

Several oxyalkylated alcohols are commercially available such as 2-(2-hexyloxyethoxy)ethanol, Ethonic TM 1214-2 alcohol ethoxylate, an alcohol ethoxylate derived from a mixture of predominantly $C_{12}$ and $C_{14}$ linear primary alcohols having an approximate degree of ethoxylation of 2, Ethonic TM 1214-3 alcohol ethoxylate, an alcohol ethoxylate derived from a mixture of predominantly $C_{12}$ and $C_{14}$ linear primary alcohols having an approximate degree of ethoxylation of 3, and Ethonic TM 1214-6.5 alcohol ethoxylate, an alcohol ethoxylate derived from a mixture of predominantly $C_{12}$ and $C_{14}$ linear primary alcohols having an approximate degree of ethoxylation of 6.5, all sold commercially by Ethyl Corporation.

Preparation of the alkoxylated tertiary amine involves the process of aminating the oxyalkylated alcohol with a secondary amine in the presence of a catalytic quantity of an amination catalyst comprising metallic iridium or metallic iridium dispersed into an inert base or support and added hydrogen at ambient pressure and at above ambient temperature.

Specific examples of secondary amines which may be used to aminate the oxyalkylated alcohols include, for example, dimethylamine, diethylamine, di-n-butylamine, di-n-decylamine, di-benzylamine, dicyclohexylamine, and diallylamine.

In general, the reaction is conducted at elevated temperature at ambient pressure in the presence of a catalytic quantity of catalyst comprising metallic iridium alone or metallic iridium dispersed on an inert support for a period of time sufficient for the nitrogen content of the reaction mixture to reach an equilibrium level. The reaction is carried out in the presence of small amounts of hydrogen.

Suitably, from about 0.0 to about 1 mole of hydrogen per mole of oxyalkylated alcohol feedstock is employed. More preferably, from about 0.3 to about 0.7 mole of hydrogen per mole of oxyalkylated alcohol is employed.

The reaction can be conducted batchwise by merely placing the catalyst in the oxyalkylated alcohol and feeding secondary amine and hydrogen while stirring at reaction temperature, or the reaction can be conducted continuously as, for example, by placing the catalyst in a packed or fluidized bed and passing the feed materials over the catalyst at reaction temperatures. When the process of the invention is conducted continuously, the desired molar ratios of oxyalkylated alcohol, hydrogen and secondary amine can be established and maintained by regulating the rates at which the feed components are fed to the reactor.

The reaction should be conducted at a temperature high enough to cause the reaction to proceed at a reasonable rate but not so high as to cause decomposition of the reactants or products. A useful range is from about 150° C. to 350° C., preferably from about 175° C. to 275° C.

The reaction should be conducted for a time sufficient to achieve the desired degree of completion of the reaction. The reaction time is not a truly independent variable but is at least dependent to some extent on the other process conditions employed. In general, higher temperatures should afford a faster reaction time while, on the other hand, lower reaction temperatures should tend to increase the time of reaction. Further, the reaction time will generally be dependent on the choice of oxyalkylated alcohols and secondary amine reactants used in the process, amount of catalyst, type of equipment used, and whether the process is continuous or batch. Good results are obtained in 1 to 8 hours with the more preferable range being from 2 to 6 hours.

The amount of catalyst employed in the process is a catalytic amount. By catalytic amount is meant an amount of catalyst sufficient to catalyze the conversion of oxyalkylated alcohol and secondary amine reactants to the corresponding alkoxylated tertiary amine compounds in comparatively high yields in a reasonable reaction time at ambient pressure and with a minimum amount of ether cleavage taking place in the starting oxyalkylated alcohol material during the reaction. In general, when unsupported metallic iridium is used in the process from about 0.01 to about 50 wt. % of the catalyst based o the weight of the starting oxyalkylated alcohol reactant is used. When a supported iridium catalyst is used, the catalyst should typically contain from about 0.1 to about 40 wt. % iridium based on the total weight of the catalyst and the remainder an inert support. A preferred range is from about 0.5 to 15 wt. %.

As mentioned above, the amination catalyst can be either metallic iridium alone, preferably in a finely divided state, or it may be used in conjunction with a relatively inert support. In the latter instance, the metal may be dispersed on a catalytic support. Suitable supports which may be employed include charcoal, alumina, diatomaceous earth, bentonite, firebrick, kaolin, ground glass, silicon carbide, silicon dioxide, kieselguhr, activated carbon, and the like. The catalyst may be employed in a finely divided form. Similarly, it can be used in particulate forms such as pellets, tablets, etc. Activated carbon is the most preferred inert support.

When an iridium metal supported catalyst is employed, such as iridium supported on activated carbon, catalyst preparation is typically effected by depositing iridium onto a high surface area activated carbon support.

The iridium may be deposited onto the base or support by any of the techniques commonly used for catalyst impregnation as, for example, impregnation from an organic or inorganic solution, precipitation, etc. Conveniently, a solution of a heat decomposable inorganic or organic iridium compound is appropriately contacted with the support material and the support is then dried and heated, the latter advantageously under reducing conditions, to form a finely dispersed iridium-containing catalyst. Illustrative of water-soluble compounds are the chloride and nitrate salts of iridium. In preparing the catalyst composition, the support material is contacted with just enough solution of iridium to wet the support so that little or no excess solution is used. This technique which insures that the desired concentration of iridium will be incorporated into the catalyst composition is known in the art and is referred to as the incipient wetness technique. After impregnating the support material, the catalyst is subjected to drying conditions to lower the water content of the resultant composition to the lowest possible level. In a typical drying procedure, the impregnated support is slowly heated from room temperature up to a temperature of, for example, approximately, 100° C. and is maintained at this temperature for at least 1 hour, and preferably from 1 to 24 hours, until all or substantially all of the water has been removed from the composition. The dried composition is then reduced with hydrogen. Reduction can be carried out by contacting the composition in a reduction zone with hydrogen at room temperature and then heating the catalyst reduction zone slowly from room temperature up to a temperature of, for example, 400° C. It is not critical that reduction of the dried catalyst composition be initiated at room temperature. Alternatively, the dried catalyst can be placed in the reduction zone immediately after drying and reduction can commence at an elevated temperature.

Commercially prepared iridium supported activated carbon catalysts are available both in the reduced and non-reduced state and can be purchased from Engelhard Industries Division, 429 Delaney Street, Newark, N.J. 07108.

The amount of secondary amine employed in the process should be at least a stoichiometric amount. This is 1.0 mole per mole of oxyalkylated alcohol. The secondary amine is preferably used in excess. A preferred amount is about 1.0 to 6.0 moles of secondary amine per mole of oxyalkylated alcohol reactant. A more preferred amount is about 1.0 to 4.0 moles of secondary amine per mole of oxyalkylated alcohol with a still more preferred amount being 1.0 to 2.0 moles of secondary amine per mole of oxyalkylated alcohol. The excess of secondary amine functions to insure maximum alkoxylated tertiary amine production.

The reaction mixture formed as a result of the reductive amination of the oxyalkylated alcohol may be recovered and fractionated in any suitable manner, such as by fractional distillation to obtain the desired alkoxylated tertiary amine product.

The following example shows how to conduct the process of the invention using iridium supported on activated carbon as the amination catalyst.

EXAMPLE I

A 250-mL creased flask equipped with a mechanical stirrer (200 rmp), water condenser (20 C), thermocouple, gas sparge tube and water trap was charged with 5.0g of a catalyst of iridium metal supported on activated carbon obtained from Engelhard Industries Division, 429 Delaney Street, Newark, N.J. 07108 containing 2.0 wt. % iridium and 100g (0.53 mole) of 2-(2-hexyloxyethoxy)ethanol. The flask was swept with nitrogen for 15 minutes and the mixture was heated under hydrogen to 220°) C. The reaction was carried out under a continuous hydrogen flow of 0.1 cf/hr. At 220° C. dimethylamine feed was initiated at a rate of 0.4 cf/hr (1.3 g/min). The reaction was stopped after 16 hours. The product was analyzed by gas chromatography to determine percent yield of alkoxylated tertiary amine product. Analysis indicated a yield of alkoxylated tertiary amine of about 53% based on a conversion of about 81% and 2 percent cleavage products. The total yield of alkoxylated amine products was about 80%.

What is claimed:

1. A method for preparing at ambient pressure an alkoxylated tertiary amine having the formula:

$$RO(R_1)_xCH_2CHNR_3R_4$$

or a mixture of such amines which comprises reacting an oxyalkylated alcohol of the formula:

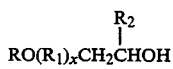

or a mixture of such alcohols, with a secondary amine of the formula $HNR_3R_4$ at elevated temperature in the presence of a catalytic quantity of an amination catalyst comprising metallic iridium in the presence of added hydrogen wherein R is a straight or branched chain alkyl group having from 1 to 20 carbon atoms, a cyclic alkyl group having from 5 to 10 carbon atoms, an aryl group having up to 12 carbon atoms, or an aralkyl or alkaryl group having up to 18 carbon atoms, $R_1$ is a single unit or a series of units of the formula:

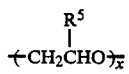

wherein in each unit $R_5$ is independently selected from the group consisting of hydrogen and a straight or branched chain alkyl group having from 1 to 12 carbon atoms and x is an integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

2. A method according to claim 1 wherein R is a straight chain alkyl group having from 8 to 16 carbon atoms, $R_1$ is a

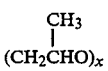

group with x being 7 and $R_2$, $R_3$ and $R_4$ are methyl groups.

3. A method according to claim 1 wherein $R_1$ is a $+CH_2CHO+_{\overline{x}}$ group, where the substituent is $CH_2CH_3$, a $(CH_2CHO)_x$ group where the substituent is $CH_2CH_2CH_3$, or a $+CH_2CHO+_{\overline{x}}$ group where the substituent is octyl.

4. A method according to claim 1 wherein the process is conducted at a temperature in the range of from about 150° C. to about 350° C.

5. A method according to claim 1 wherein said catalyst is present in an amount of from about 0.1 to about 50 wt. % based on the weight of the starting oxyalkylated alcohol reactant.

6. A method according to claim 1 wherein said metallic iridium is dispensed in a relatively inert support.

7. A method according to claim 6 wherein said supported iridium contains about 0.1 to about 40 wt. % iridium.

8. A method according to claim 7 wherein said inert support is activated carbon.

9. A method according to claim 8 wherein the amount of hydrogen present is about 0.3 to 0.7 moles of hydrogen per mole of said oxyalkylated alcohol.

* * * * *